(12) United States Patent  
Koyama (10) Patent No.: US 8,434,351 B2
(45) Date of Patent: May 7, 2013

(54) SENSING INSTRUMENT (75) Inventor: Mitsuaki Koyama, Sayama (JP)

(73) Assignee: Nihon Dempa Kogyo Co., Ltd, Tokyo (JP)

( * ) Notice: Subject to any disclaimer, the term of this patent is extended or adjusted under 35 U.S.C. 154(b) by 668 days.

(21) Appl. No.: 12/448,160

(22) PCT Filed: Dec. 25, 2007

(86) PCT No.: PCT/JP2007/075354
§ 371 (c)(1),
(2), (4) Date: Jun. 11, 2009

(87) PCT Pub. No.: WO2008/078832
PCT Pub. Date: Jul. 3, 2008

(65) Prior Publication Data
US 2010/0024532 A1 Feb. 4, 2010

(30) Foreign Application Priority Data

Dec. 25, 2006 (JP) ................................ 2006-346875

(51) Int. Cl.
*G01N 29/00* (2006.01)
(52) U.S. Cl.
USPC ....................................... 73/61.49; 73/61.79
(58) Field of Classification Search ............. 73/579, 73/61.49, 61.45, 61.75, 61.79
See application file for complete search history.

(56) References Cited

U.S. PATENT DOCUMENTS

| 5,675,296 A | 10/1997 | Tomikawa | |
|---|---|---|---|
| 2004/0263270 A1* | 12/2004 | Hashimoto | 331/117 R |
| 2005/0179543 A1* | 8/2005 | Lian et al. | 340/540 |
| 2008/0156097 A1* | 7/2008 | Onishi et al. | 73/579 |

FOREIGN PATENT DOCUMENTS

| EP | 1788377 A1 * | 5/2007 |
| JP | 8-307199 | 11/1996 |
| JP | 2004-294356 | 10/2004 |
| JP | 2004-320321 | 11/2004 |
| JP | 2006-029870 | 2/2006 |
| JP | 2006184260 A * | 7/2006 |
| JP | 2006-258787 | 9/2006 |
| WO | WO-2006/016721 | 2/2006 |

* cited by examiner

*Primary Examiner* — Daniel Larkin
*Assistant Examiner* — Jamar Ray
(74) *Attorney, Agent, or Firm* — Jordan and Hamburg LLP (57) ABSTRACT

A sensing instrument using a piezoelectric resonator changes natural frequency when coming into contact with a liquid to adsorb a substance to be sensed in the liquid. The sensing instrument includes an oscillator circuit supplying a piezoelectric resonator with oscillation driving power for oscillating the piezoelectric resonator so as to set a driving current to 0.3 mA or less. A measuring unit measures a concentration of the substance to be sensed based on an oscillation output of the oscillator circuit. Self-heating of the piezoelectric resonator is suppressed. Consequently, a change of the oscillation frequency of the piezoelectric oscillator is suppressed, which as a result enables accurate detection of a variation of the frequency due to the adsorption of the substance to be sensed.

2 Claims, 12 Drawing Sheets

SENSING INSTRUMENT

TECHNICAL FIELD

The present invention relates to a sensing instrument which uses a piezoelectric resonator, for example, a quartz resonator having, on its front surface, an adsorption layer for adsorbing a substance to be sensed and changing in natural frequency when coming into contact with a liquid to adsorb the substance to be sensed in the liquid and which detects a variation of the natural frequency of the piezoelectric resonator to sense the substance to be sensed in the liquid.

BACKGROUND ART

As a method for sensing a trace substance, a sensing instrument using a quartz resonator has been known. This sensing instrument has a quartz sensor in which an adsorption layer for adsorbing a substance to be sensed is formed on a front surface of the quartz resonator, and measures the presence/absence or concentration of the substance to be sensed by utilizing the fact that when the quartz resonator, more particularly, the adsorption layer adsorbs the substance to be sensed, its natural frequency changes according to an adsorption amount of the substance to be sensed, and this sensing instrument is advantageous in that it is applicable to a wide range and has a simple structure as an instrument, and moreover, is capable of measuring even an extremely minute amount of substance because of its high sensitivity. Therefore, in the analysis of a disease marker substance contained in blood, urine, and the like, it has conventionally been expected that a method using the quartz sensor will be an effective method replacing a conventional method.

The present inventor has been studying the possibility of applying a quartz sensor to, for example, dioxin and PCB which are environmental pollutants, a disease marker in blood, or the like, and this method, if achieving high-precision measurement of a target substance, would be innovative. The reason is because a method using a gas-chromatography mass spectrometer and an ELISA method (enzyme-linked immunosorbent assay method), which are currently known as methods of measuring, for example, dioxin, have the following problems. The former requires an extremely high instrument cost and thus a considerably high analysis cost and takes a long period of time for analysis, and the latter is low in analysis precision, though requiring less instrument cost and analysis cost and taking a shorter period of time for analysis compared with the gas-chromatography mass spectrometer.

Incidentally, a sensing instrument using a quartz sensor, if not requiring very high measurement precision, is not difficult to manufacture, but if requiring high measurement precision, it is practically difficult to manufacture. The reason is that it is very difficult to detect a minute frequency change accurately and in a short time, and besides the adsorption of a substance to be sensed, there are many disturbance factors for frequency fluctuation.

Under such circumstances, the present applicant has developed an art in which a frequency signal of an oscillator circuit is converted to a digital signal, a sinusoidal signal specified by the digital signal is subjected to quadrature detection, a rotation vector rotating at a velocity according to a frequency difference between the sinusoidal signal and a sinusoidal signal used for the detection is prepared, and the velocity of this rotation vector is monitored, whereby making it possible to detect a frequency change with extremely high precision (patent document 1). However, the higher the sensitivity of the frequency change detection, the greater an influence that the disturbance gives to a measurement error.

Figure 11:
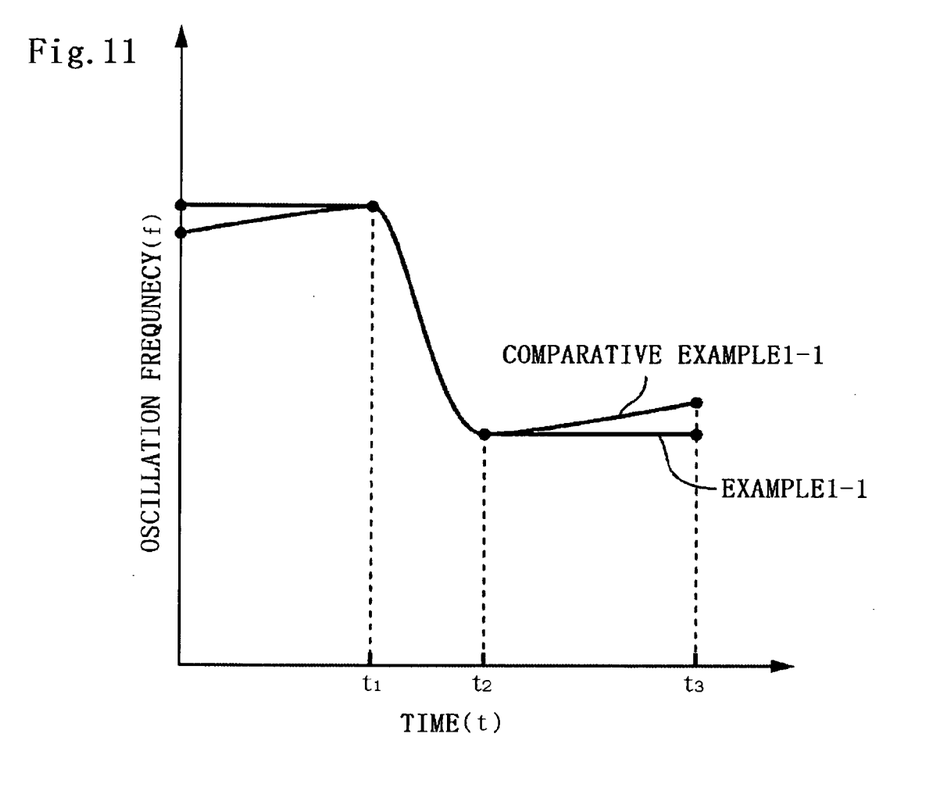
FIG. 11 is a characteristic chart showing states of an oscillation frequency of the quartz resonator before and after an antigen-antibody reaction.
Figure 12:
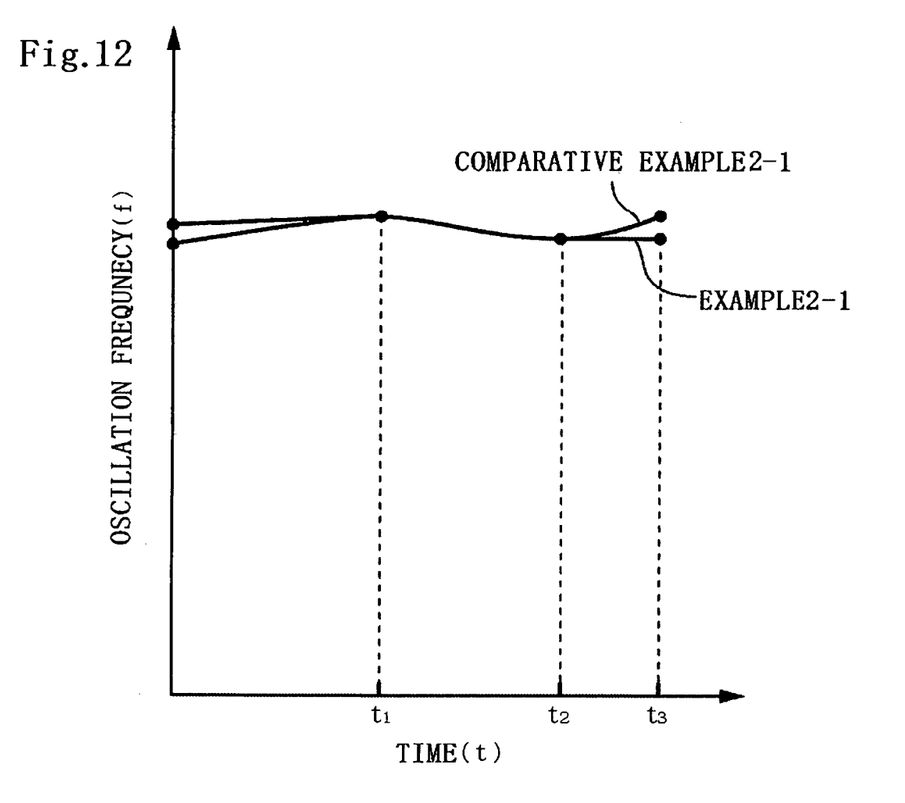
FIG. 12 is a characteristic chart showing states of the oscillation frequency of the quartz resonator before and after the antigen-antibody reaction.

In the use of the above-described rotation vector method, when pure water is first supplied into a sensing sensor including a quartz resonator, followed by the supply of a sample solution containing an antigen as a substance to be sensed, an antibody layer which is an adsorption layer provided on a quartz resonator causes an antigen-antibody reaction with the antigen to capture the antigen, so that a frequency lowers as shown in FIG. 11 and FIG. 12 described in later-described experimental examples. However, it is observed that the frequency tends to gradually increase during the measurement, which makes it difficult to detect an end point of the frequency after the supply of the sample solution, and especially when the antigen concentration is low and thus the frequency change is small, there is a problem of difficulty in detecting the end point of the frequency.

Figure 14:
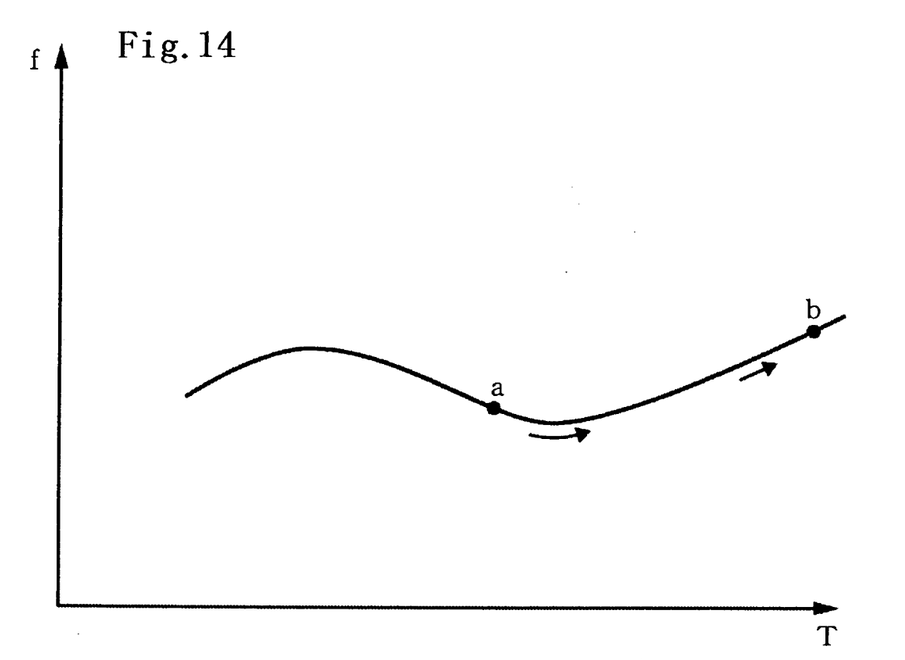
FIG. 14 is a characteristic chart showing a frequency-temperature characteristic.

As a result of a pursuit of a cause of the above, the present inventor has come to the conclusion that this is due to self-heating of a quartz piece as is inferred from the later-described experimental examples. Specifically, when the quartz resonator is oscillated in the liquid, an equivalent series resistance of the quartz piece becomes as large as, for example, 150 ohm, so that a driving current flows in the quartz piece, which results in its self-heating. Here, FIG. 14 is a frequency-temperature characteristic chart of the quartz resonator, and it is thought that due to the self-heating of the quartz resonator, the frequency tries to move, for example, from point a to point b along a characteristic curve which is a cubic curve, resulting in a change in the frequency. The phenomenon that the frequency gradually increases is consistent with that the temperature slides in a downstream-side portion of the cubic curve in FIG. 14, and the frequency as a result increases along this curve.

Therefore, even if a high-precision method is adopted for the frequency, there is a problem that its advantage cannot be fully utilized.

Patent document 1

Japanese Patent Application Laid-open No. 2006-258787

DISCLOSURE OF THE INVENTION

The present invention was made under such circumstances, and has an object to provide a sensing instrument using a piezoelectric resonator such as a quartz resonator which changes in natural frequency when coming into contact with a liquid to adsorb a substance to be sensed in the liquid, the sensing instrument having a suppressed adverse effect accompanying improvement in precision of detection sensitivity of a frequency change.

The present invention is a sensing instrument which uses a piezoelectric resonator having, on a front surface thereof, an adsorption layer for adsorbing a substance to be sensed and changing in natural frequency when coming into contact with a liquid to adsorb the substance to be sensed in the liquid and which senses the substance to be sensed in the liquid based on a change in the natural frequency of the piezoelectric resonator, the sensing instrument including:

an oscillator circuit supplying the piezoelectric resonator with oscillation driving power for oscillating the piezoelectric resonator so as to set a driving current to 0.3 mA or less; and a measuring unit measuring a concentration of the substance to be sensed based on an oscillation output of the oscillator circuit. Incidentally, when the liquid comes into contact with the piezoelectric resonator, an equivalent series resistance of the piezoelectric resonator becomes, for example, as high as 150Ω or more.

According to the present invention, when the liquid comes into contact with the piezoelectric resonator, the equivalent series resistance of the piezoelectric resonator becomes high, but since the driving current for oscillating the piezoelectric resonator is set to 0.3 mA or less, it is possible to suppress the self-heating of the piezoelectric resonator as shown in the later-described examples. Consequently, a change in the oscillation frequency of the piezoelectric resonator is suppressed, and as a result, it is possible to accurately detect a variation of the frequency due to the adsorption of the substance to be sensed, enabling high-precision measurement of the concentration of the substance to be sensed.

BEST MODE FOR CARRYING OUT THE INVENTION

Figure 1:
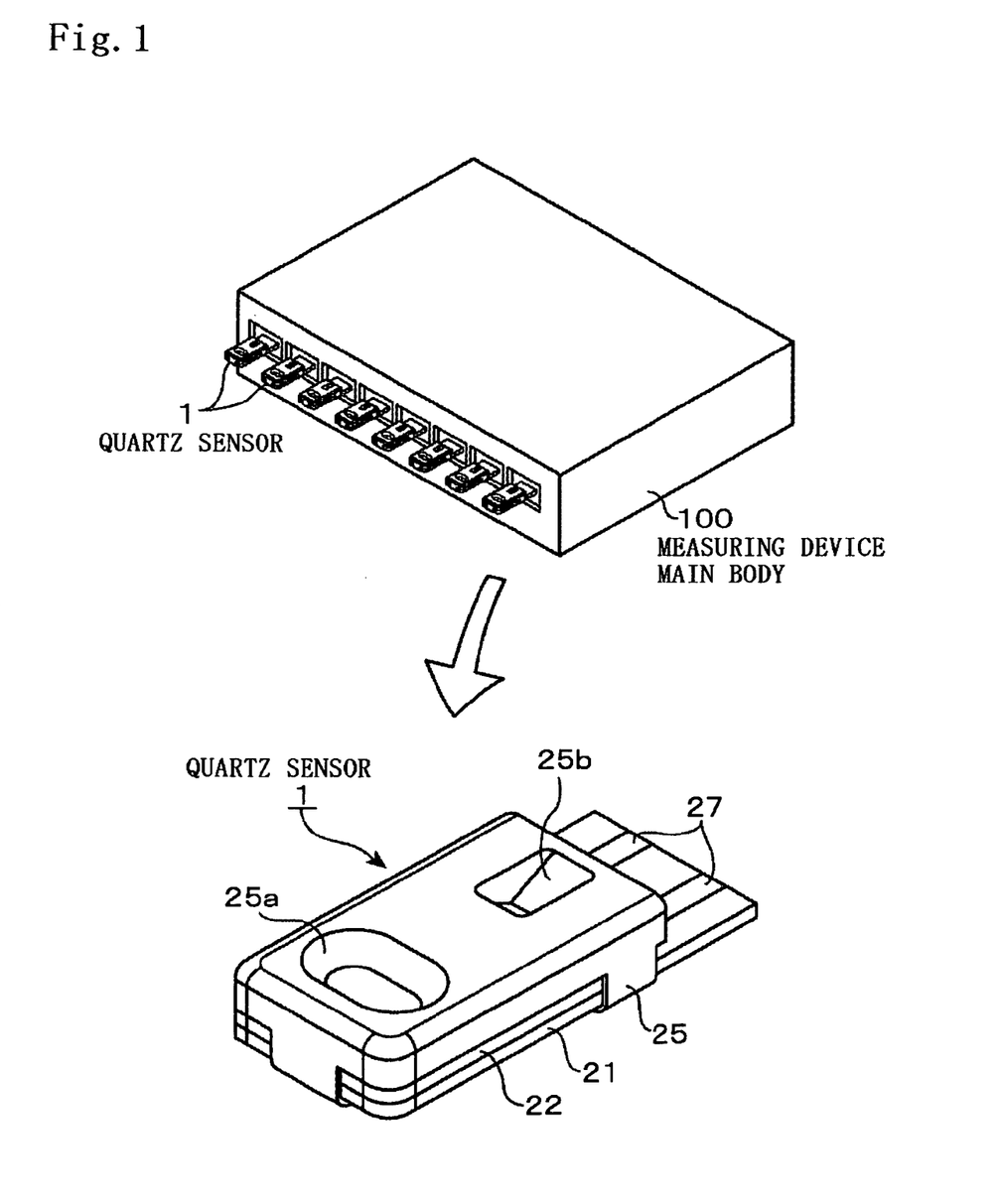
FIG. 1 is a perspective view showing the outer appearance of an embodiment of a sensing instrument including a quartz sensor according to the present invention.
Figure 2:
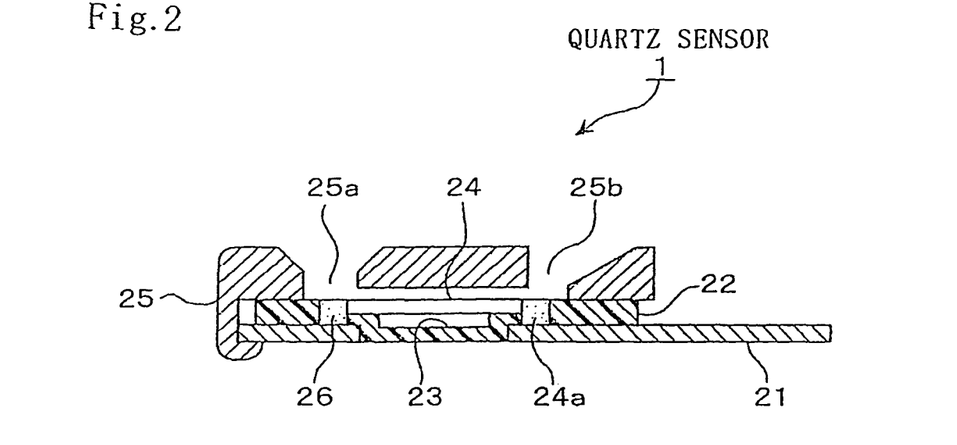
FIG. 2 is a schematic sectional view showing a quartz sensor used in the embodiment.

Hereinafter, an embodiment of a sensing instrument according to the present invention will be described. First, the whole structure of the sensing instrument will be described. As shown in FIG. 1, the sensing instrument includes a plurality of, for example, eight quartz sensors 1 and a measuring device main body 100 to which the quartz sensors 1 are attachably/detachably mounted. As shown in FIG. 1 and FIG. 2, the quartz sensor 1 includes a printed circuit board 21 which is a wiring board, a rubber sheet 22 stacked on the printed circuit board 21, a quartz resonator 24 as a piezoelectric resonator provided to close a recessed portion 23 provided in the rubber sheet 22, and an upper cover case 25 mounted from above the rubber sheet 22. As the quartz resonator 24 used in this embodiment, the quartz resonator 24 whose oscillation frequency is 1 to 30 MHz, in this example, 9.176 MHz is used, for instance. In the upper cover case 25, an injection port 25a for a sample solution and a check port 25b for the sample solution are formed, and the sample solution is injected from the injection port 25a, so that a space on an upper surface side of the quartz resonator 24 is filled with the sample solution. The recessed portion 23 forms an airtight space on a lower surface side of the quartz resonator 24, whereby a Languban-type quartz sensor is formed.

Figure 3:
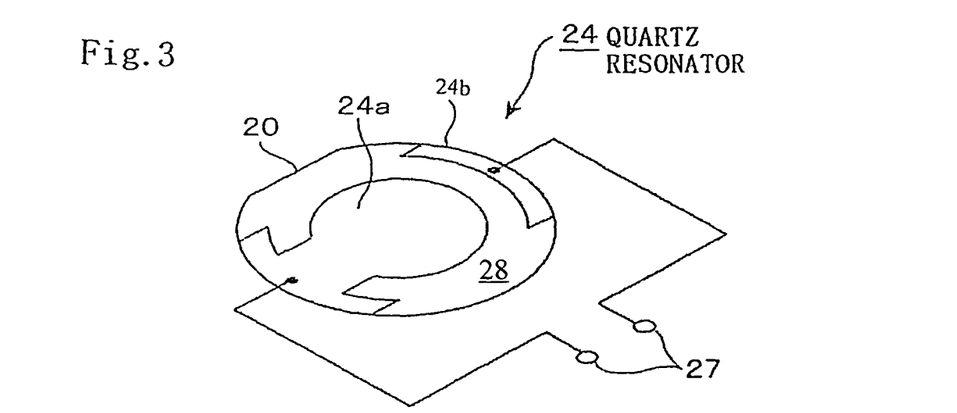
FIG. 3 is an explanatory view showing a quartz resonator used in the embodiment and peripheral wiring.

As shown in FIG. 3, in the quartz resonator 24, electrodes, 24a, 24h are provided respectively on both surfaces of a quartz piece 20 in, for example, a circular shape (the rear surface-side electrode 24h is formed continuously from a front surthce-side peripheral edge portion). These electrodes 24a, 24b are electrically connected via conductive adhesives 26 to printed wirings 27, respectively, which are a pair of conductive paths provided in the hoard 21. On one surface of the quartz resonator 24, for example, on a front surface of the electrode 24a, an adsorption layer 28 for adsorbing a substance to be sensed is formed.

Next, an internal circuit of the measuring device main body 100 will be described by using FIG. 4. 4 in FIG. 4 denotes an oscillator circuit for oscillating the quartz resonator 24 of the quartz sensor 1, and a measuring unit 6 is connected on a subsequent stage of the oscillator circuit 4 via a buffer amplifier 5. The oscillator circuit 4 is structured as a Colpitts oscillator circuit, in which Tr denotes a transistor as an oscillation amplifying element, 40 and 41 denote capacitors forming divided capacitive components, and Vcc denotes a constant voltage source. As for other portions, 42 to 44 denote capacitors and 45 to 48 denote resistors. Further, 49 denotes terminal portions to which the quartz sensor 1 is attachably/detachably connected, and are provided in the measuring device main body 100 shown in FIG. 1. In the oscillator circuit 4, a circuit constant is set so that a driving current of the quartz piece 20 becomes 0.3 mA or less. Concretely, by the adjustment of resistance values of the resistors 45, 46, 47 shown in FIG. 4, the driving current is set to 0.3 mA or less.

The measuring unit 6 is capable of measuring a frequency of the oscillation output by using the method using the rotation vector described in the aforesaid patent document 1, for instance, and may include, for example, a frequency counter, an arithmetic part calculating a variation of the counter number, and so on. An example of a concrete circuit configuration of the measuring unit 6 will be described later.

Figure 4:
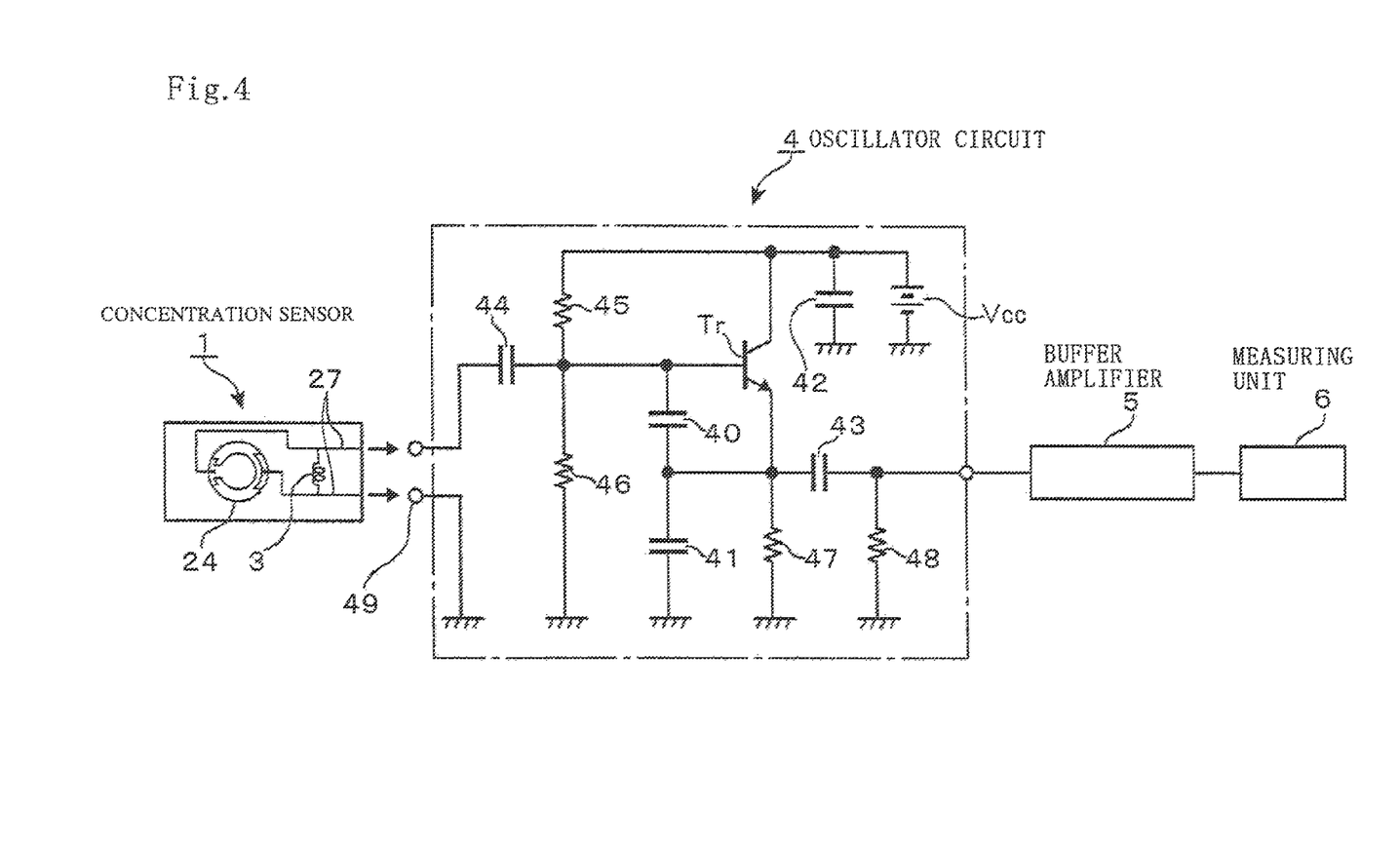
FIG. 4 is a block circuit diagram showing the sensing instrument of the embodiment.

Incidentally, in this example, an eight-channel structure with the eight quartz sensors 1 mounted is adopted, and the circuit shown in FIG. 4 is prepared for each of the eight channels, and an output of a channel whose output is connected to the measuring unit 6 is switched among these channels.

Figure 5:
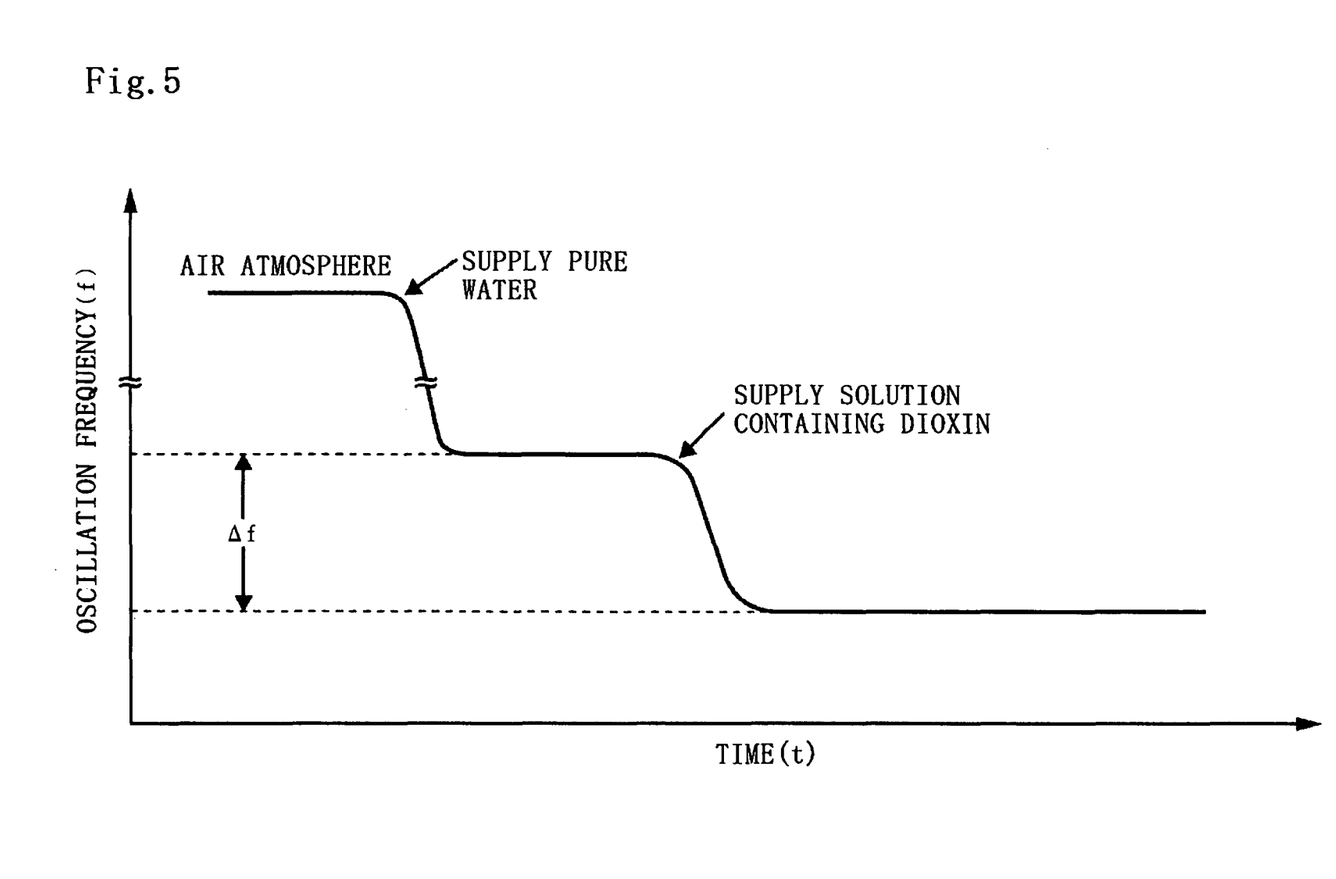
FIG. 5 is an explanatory chart showing an operation procedure of the sensing instrument.

Next, the operation of the sensing instrument will be described with reference to FIG. 5. First, the quartz sensor 1 (see FIG. 1) is inserted to the measuring device main body 100 and a solution, for example, pure water not containing a substance to be sensed is filled in the quartz sensor 1 in order to find a blank value, for instance. When the pure water is filled in the quartz sensor 1, a value of the equivalent series resistances of the quartz piece 20 becomes about 150Ω to 500Ω, for instance. Then, the oscillator circuit 4 applies oscillation driving power to the quartz piece 20 so that the driving current of the quartz piece 20 becomes 0.3 mA or less, for example, 0.2 mA. Since viscosity of the pure water at this time is higher than that of an air atmosphere, the pure water adheres to a quartz surface, so that the oscillation frequency of the quartz resonator 24 becomes lower than that when the quartz resonator 24 is oscillated in the air atmosphere, as shown in FIG. 5. Next, while the 0.2 mA oscillation driving power is applied to the quartz piece 20, a solution containing a substance to be sensed, for example, dioxin is injected into the pure water in the quartz sensor 1. The dioxin is captured by the adsorption layer on the front surface of the quartz resonator 24 because an anti-dioxin antibody selectively captures molecules, and the oscillation frequency of the quartz resonator 24 changes by Δf according to an amount of the adsorption as shown in FIG. 5. As will be described in the later-described experimental examples, after the oscillation frequency of the quartz resonator 24 changes due to the antigen-antibody reaction, the frequency stabilizes without gradually increasing. Then, the oscillation frequency of the quartz resonator 24 at this time is found to find Δf, and the concentration of the dioxin is found based on a pre-found relational expression (calibration curve) showing the relation between Δf and the concentration of dioxin. The concentration is displayed on a not-shown display part, for instance. Incidentally, based on the comparison between the detected concentration and a preset concentration, "present" may be output if the detected concentration is higher than the set concentration, and "absence" may be output when the detected concentration is lower than the set concentration.

According to the above-described embodiment, since the driving current for oscillating the quartz resonator 24 is set to 0.3 mA or less, in this example, to 0.2 mA, it is possible to suppress the self-heating of the quartz resonator 24 as shown in the later-described experimental examples even if the quartz resonator 24 comes into contact with the liquid to have an increased equivalent series resistance. This can suppress the change in the oscillation frequency of the quartz resonator 24, and as a result, makes it possible to accurately detect a variation of the frequency due to the adsorption of the substance to be sensed, in this example, dioxin, enabling high-precision measurement of the concentration of the dioxin. This invention is effective especially for an instrument having extremely high detection sensitivity like the rotation vector type, since the self-heating of the quartz resonator 24 is also reflected in frequency detection data.

Incidentally, the substance to be sensed may be, for example, disease marker protein, a bacteria of infectious disease, PCB, or the like.

Figure 6:
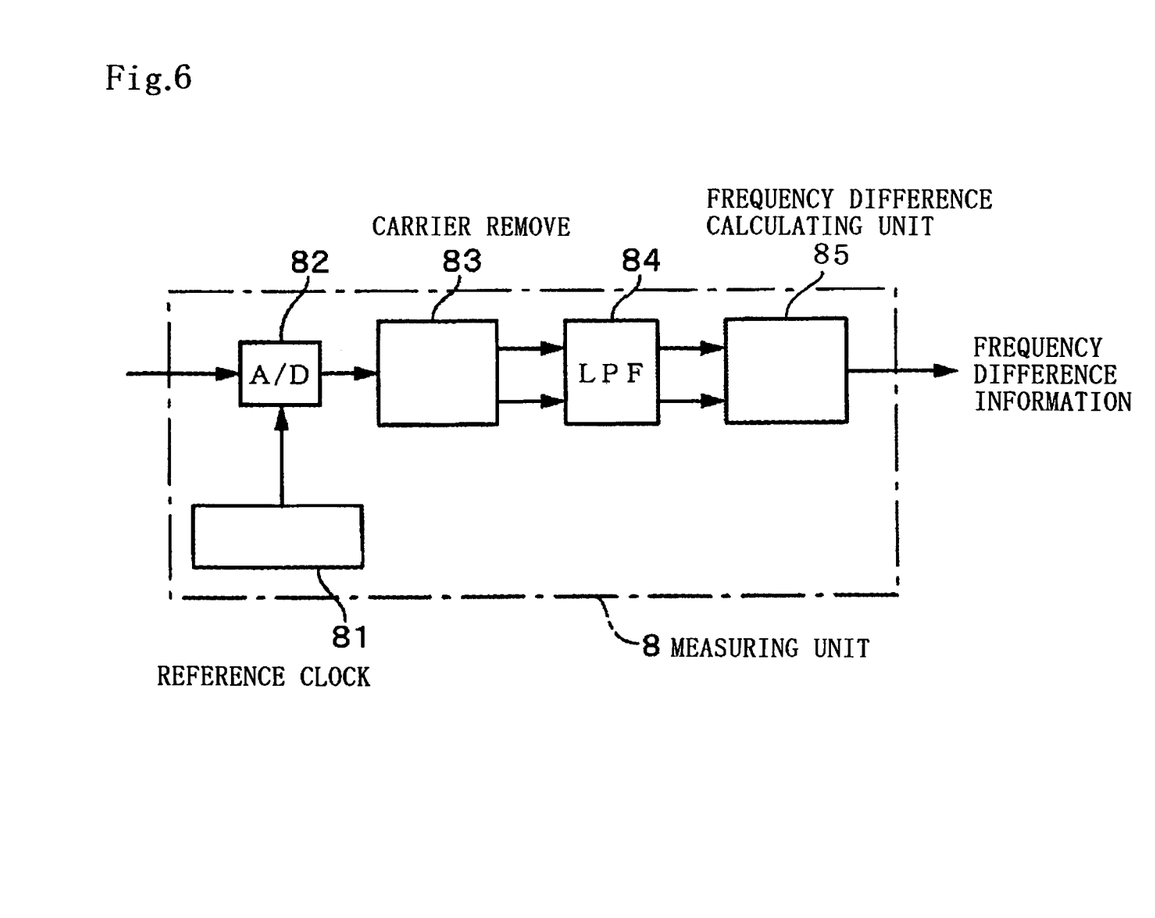
FIG. 6 is a block diagram showing an example of a measuring unit.

Here, an example of the above-described measuring unit 6 is shown in FIG. 6. In FIG. 6, 81 denotes a reference clock generating unit, and it outputs a clock signal, which is a frequency signal with extremely stable frequency, in order to sample the frequency signal from the switching unit 5. 82 denotes an A/D (analog/digital) converter, and it samples the frequency signal based on the clock signal from the reference clock generating unit 81 and outputs the sampling value as a digital signal. For example, a frequency fc of the frequency signal and a sample frequency (frequency of the clock signal) fs can be set to 11 MHz and 12 MHz respectively. In this case, a fundamental wave of the frequency signal specified by the output signal being the digital signal from the A/D converter 61 is a 1 MHz sinusoidal wave.

On a subsequent stage of the A/D converter 82, a carrier remove 83 and a low-pass filter 84 are provided in this order. The carrier remove 83 and the low-pass filter 84 are used to extract a rotation vector which rotates at a frequency corresponding to a difference between, for example, the frequency of the 1 MHz sinusoidal signal specified by the digital signal from the A/D converter 82 and the frequency of a sinusoidal signal used for quadrature detection.

Figure 7:
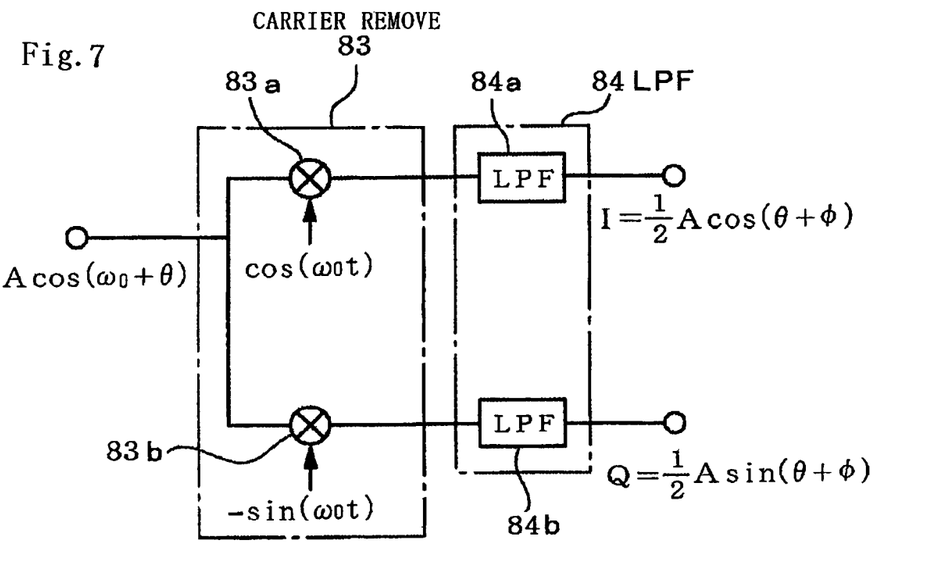
FIG. 7 is a block diagram showing part of the circuit block shown in FIG. 6.

For easier explanation of the operation of extracting the rotation vector, the sinusoidal signal specified by the digital signal from the A/D converter 82 is defined as A cos(ω0t+θ). As shown in FIG. 7, the carrier remove 83 includes a multiplying unit 83a multiplying the sinusoidal signal by cos(ω0t) and a multiplying unit 83b multiplying the sinusoidal signal by −sin(ω0t). That is, by such arithmetic operation, the quadrature detection is performed. An output of the multiplying unit 83a and an output of the multiplying unit 83b are expressed by an expression (2) and an expression (3) respectively.

$$A\cos(\omega 0t + \theta) \cdot \cos(\omega 0t) = \\ 1/2 \cdot A\cos\theta + 1/2\{\cos(2\omega 0t) \cdot \cos\theta + \sin(2\omega 0t) \cdot \sin\theta\} \quad (2)$$

$$A\cos(\omega 0t + \theta) \cdot -\sin(\omega 0t) = \\ 1/2 \cdot A\sin\theta - 1/2\{\sin(2\omega 0t) \cdot \cos\theta + \cos(2\omega 0t) \cdot \sin\theta\} \quad (3)$$

Therefore, when the output of the multiplying unit 83a and the output of the multiplying unit 83b are passed through low-pass filters 84a and 84b respectively, the 2ω0t frequency signal is filtered out, and as a result, ½·A cos θ and ½·A sin θ are extracted from the low-pass filter 84.

Then, when the frequency of the sinusoidal signal expressed as A cos(ω0t+θ) changes, A cos(ω0t+θ) becomes A cos(ω0t+θ+ω1t). Note that ω1 is sufficiently smaller than ω0. Therefore, ½·A cos θ becomes ½·A cos(θ+ω1t), and ½·A sin θ becomes ½·A sin(θ+ω1t). That is, the output obtained from the low-pass filter 84 is a signal corresponding to a variation ω½π of the frequency of the sinusoidal signal [A cos(ω0t+θ)]. That is, these values are a real part (I) and an imaginary part (Q) which are complex expression of the rotation vector rotating at the frequency corresponding to the difference between the frequency of the sinusoidal signal specified by the digital signal from the A/D converter 82 and the frequency ω0/2π of the sinusoidal signal used for the quadrature detection.

Figure 8:
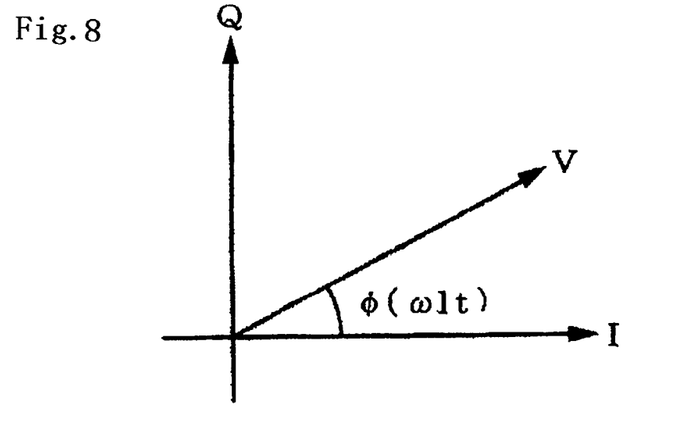
FIG. 8 is an explanatory chart showing a rotation vector extracted by the block diagram shown in FIG. 7.

FIG. 8 is a chart showing this rotation vector and an angular velocity of this rotation vector is ω1. Therefore, if there is no change in the frequency of the sinusoidal signal, ω1t is zero and thus the rotation speed of the rotation vector is zero, but when due to the adsorption of the substance to be sensed by the quartz resonator 24, the frequency of the quartz resonator changes and accordingly the frequency of the sinusoidal signal changes, the rotation vector rotates at the rotation speed corresponding to the variation.

Incidentally, the angular velocity corresponding to the oscillation frequency of the quartz resonator in the absence of a substance to be sensed rarely agrees with the angular velocity of the sinusoidal signal used for the quadrature detection, and therefore, in actual practice, the angular velocity of the rotation vector corresponding to the oscillation frequency of the quartz resonator in the absence of the substance to be sensed and the angular velocity of the rotation vector corresponding to the oscillation frequency of the quartz resonator in the presence of the substance to be sensed are found, and a difference between the angular velocities is found. The difference between the angular velocities of the rotation vector is a value corresponding to the variation of the frequency of the quartz resonator caused by the adsorption of the substance to be sensed by the quartz resonator.

EXAMPLES

Next, experiments conducted in order to confirm the effects of the present invention will be described.

Experimental Example 1

Figure 9:
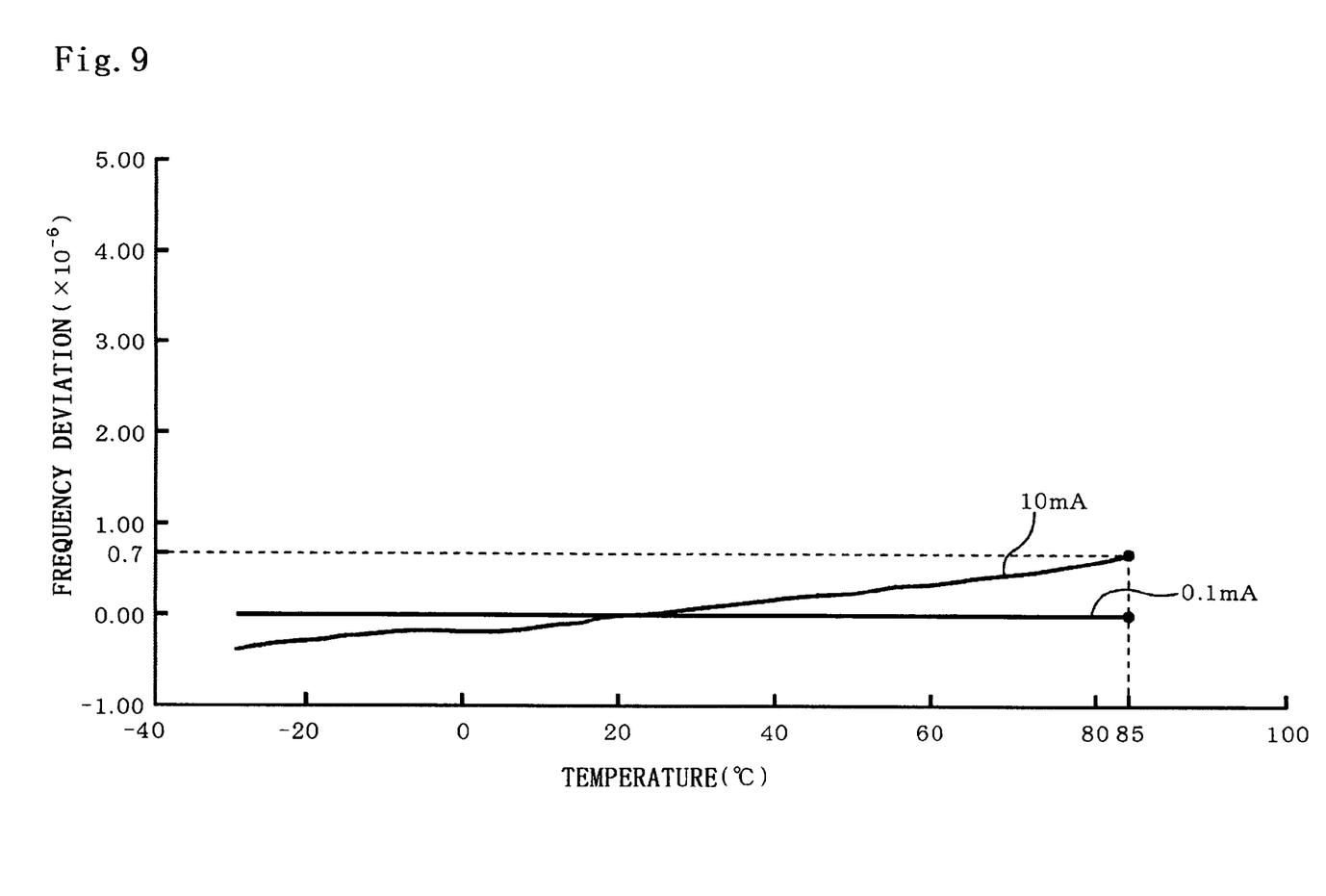
FIG. 9 is a characteristic chart showing a difference between a frequency-temperature characteristic when a driving current is 10 mA and a reference frequency-temperature characteristic when the driving current is 0.1 mA.
Figure 10:
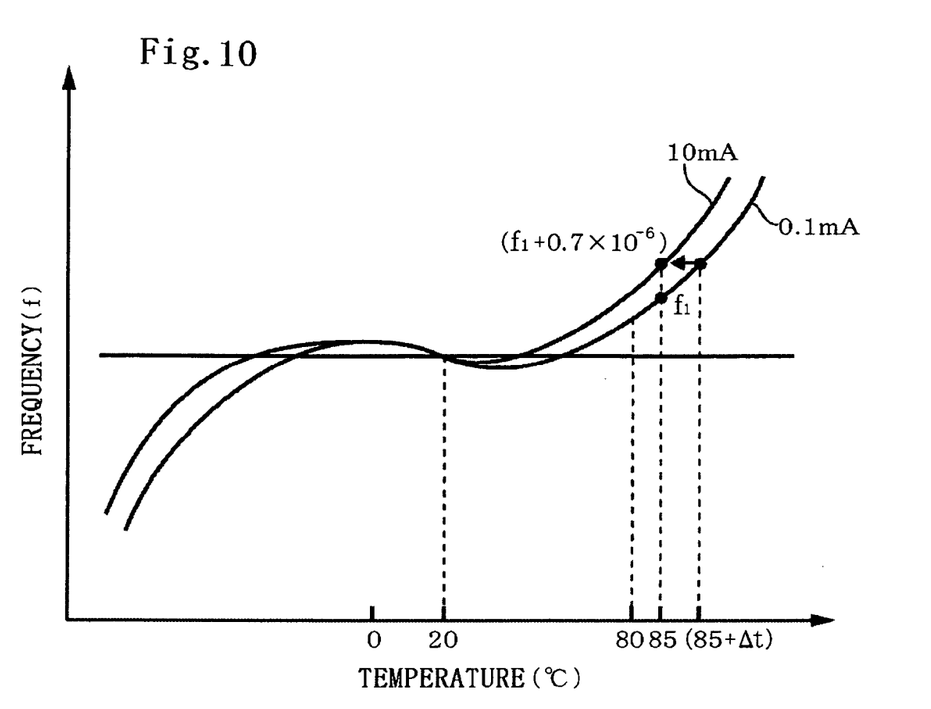
FIG. 10 is a characteristic chart showing a frequency-temperature characteristic.

The experiment was conducted in order to find a frequency-temperature characteristic of the quartz resonator 24, under various driving currents, and data obtained when the driving current was 10 mA among the obtained data was studied. FIG. 9 shows a difference between the frequency-temperature characteristic when the driving current is 10 mA and a reference frequency-temperature characteristic when the driving current is 0.1 mA. FIG. 10 shows the frequency-temperature characteristic when the driving current is 0.1 mA and the frequency-temperature characteristic when the driving current is 10 mA. It is understood from FIG. 9 that the frequency at 85° C. when the driving current is 10 mA is $f1+0.7\times10^{-6}$, where f1 is the frequency at 85° C. when the driving current is 0.1 mA as shown in FIG. 10. The $f1+0.7\times10^{-6}$ frequency is detected at the temperature of $(85+\Delta t)°$ C. when the driving current is 0.1 mA, while it is detected at the temperature of 85° C. when the driving current is 10 mA. Therefore, when the driving current is large, the frequency-temperature characteristic apparently deviates toward a lower temperature side (left in FIG. 10) as shown in FIG. 10. That is, as shown in FIG. 10, it has been found out that when the driving current is 10 mA, the frequency ($f1+0.7\times10^{-6}$) which should be detected at the temperature of $(85+\Delta t)°$ C. is detected at the temperature of 85° C. That is, even though an ambient temperature is 85°, the frequency of the quartz resonator 24 is a value corresponding to the $(85+\Delta t)°$ C. temperature. It is inferred that this is because the temperature increases by $\Delta t$ due to the self-heating (internal heating) of the driven quartz resonator 24. Therefore, it can be said that an increase in the driving current causes an increase in the internal temperature of the quartz resonator 24.

Experimental Example 2

Example 1-1

In the measurement of a substance to be sensed using the above-described sensing instrument, a predetermined amount of pure water was supplied into the quartz sensor 1, and the oscillation driving power was applied so that the driving current of the quartz piece 20 became 0.2 mA. Subsequently, a predetermined amount of a PBS solution (a phosphoric acid buffer solution) containing 100 µg/ml of a CRP antibody was injected into the pure water in the quartz sensor 1 while the 0.2 mA driving current was applied to the quartz piece 20. Then, states of the oscillation frequency of the quartz resonator 24 before and after the antigen-antibody reaction were observed. The states are shown in FIG. 11. Note that in this measurement, the quartz resonator 24 with a 9.176 MHz oscillation frequency is used.

Comparative Example 1-1

The substance to be sensed was measured with the same supply amounts of the pure water and the sample solution as those of the example 1-1, except that the oscillation driving power was adjusted so that the driving current of the quartz piece 20 became 0.5 mA. Then, states of the oscillation frequency of the quartz resonator 24 before and after the antigen-antibody reaction were observed. The states are shown in FIG. 11.

Example 2-1

The substance to be sensed was measured with the same supply amount of the pure water and the same value of the driving current as those of the example 1-1, except that a predetermined amount of the PBS solution containing a 10 µg/ml CRP antibody was injected into the pure water in the quartz sensor 1. Then, states of the oscillation frequency of the quartz resonator 24 before and after the antigen-antibody reaction were observed. The states are shown in FIG. 12.

Comparative Example 2-1

The substance to be sensed was measured with the same supply amounts of the pure water and the sample solution as those of the example 2-1, except that the driving current was adjusted to 0.5 mA. Then, states of the oscillation frequency of the quartz resonator 24 before and after the antigen-antibody reaction were observed. The states are shown in FIG. 12.
(Results and Discussion)

In FIG. 11 and FIG. 12, oscillation frequency f is taken on the vertical axis and time t is taken on the horizontal axis. Note that the aforesaid sample solution was injected into the pure water in the quartz sensor 1 at time t1 in FIG. 11 and FIG. 12. As shown in FIG. 11 and FIG. 12, after a change of the oscillation frequency of the quartz resonator 24 due to the antigen-antibody reaction is finished, the oscillation frequency of the quartz resonator 24 from time t2 to time t3 is substantially stable in the example 1-1 and the example 2-1, while it gradually increases in the comparative example 1-1 and the comparative example 2-1. Further, as shown in FIG. 12, it is seen that the frequency change is very small in the example 2-1 and the comparative example 2-1 since the antigen concentration is low. Therefore, by adjusting the driving current to 0.2 mA, it is possible to accurately measure a difference between the oscillation frequency of the quartz resonator 24 before the antigen-antibody reaction and the oscillation frequency of the quartz resonator 24 after the antigen-antibody reaction.

Working Example 3

Working Example 3-1

In the above-described sensing instrument, the drive current was adjusted to 0.1 mA to oscillate the quartz resonator 24 in the ambient atmosphere at 25° C., and the oscillation frequency of the quartz resonator 24 in this situation was measured. Note that in this measurement, a quartz resonator 24 with a 9.176 MHz oscillation frequency was used.

Working Example 3-2

The oscillation frequency of the quartz resonator 24 was measured in the same manner as in Working Example 3-1, except that the driving current was adjusted to 0.2 mA.

Working Example 3-3

The oscillation frequency of the quartz resonator 24 was measured in the same manner as in Working Example 3-1, except that the driving current was adjusted to 0.3 mA.

Comparative Example 3-1

The oscillation frequency of the quartz resonator 24 was measured in the same manner as in Working Example 3-1, except that the driving current was adjusted to 0.5 mA.

Comparative Example 3-1

The oscillation frequency of the quartz resonator 24 was measured in the same manner as in Working Example 3-1, except that the driving current was adjusted to 7.0 mA.

(Results and Discussion)

Figure 13:
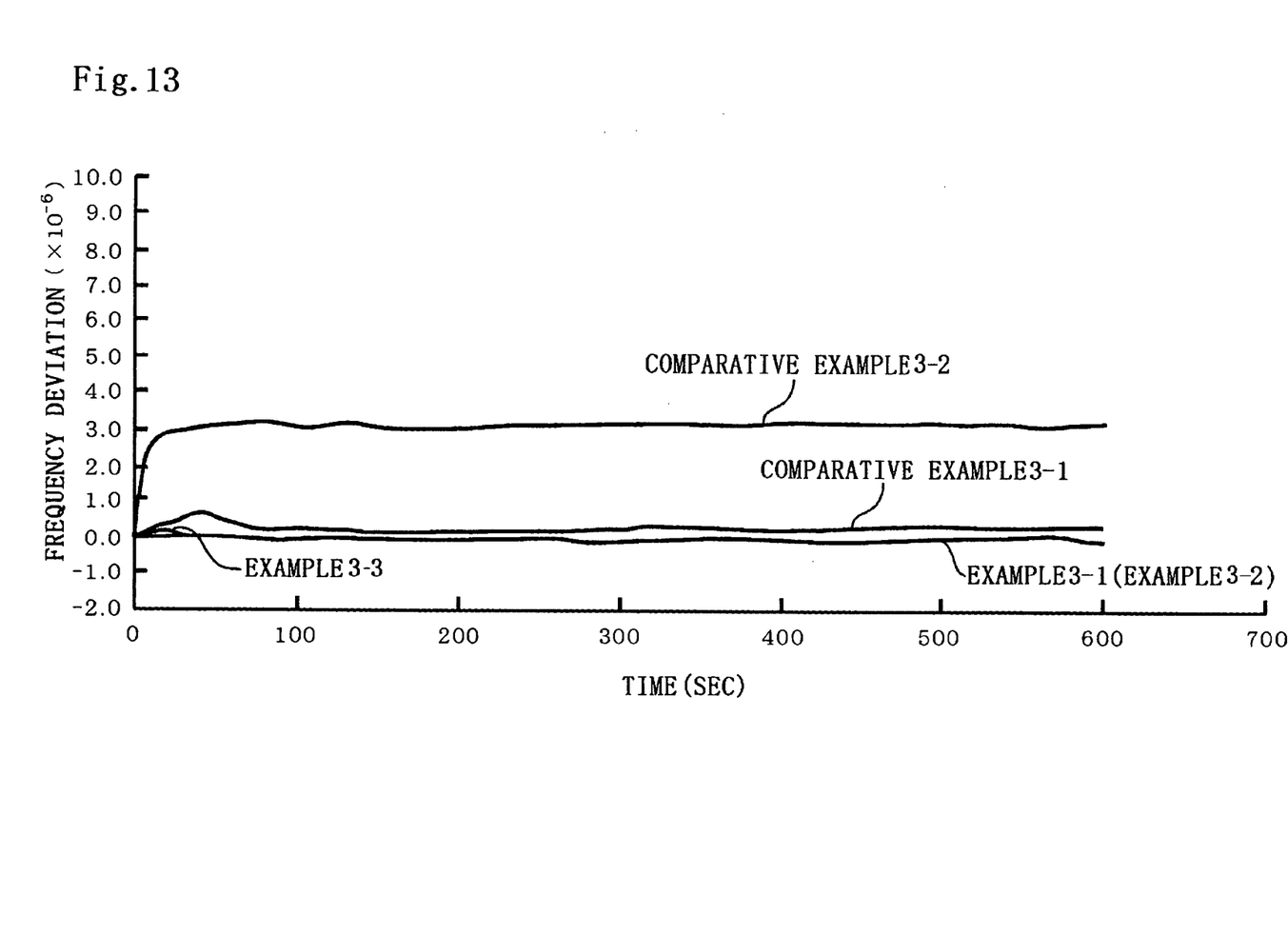
FIG. 13 is a characteristic chart showing a frequency-time characteristic.

FIG. 13 is a characteristic chart showing frequency-time characteristics of the example 3-1, the example 3-2, the example 3-3, the comparative example 3-1, and the comparative example 3-2 in the air atmosphere at 25° C. In FIG. 13, frequency deviation ($\times 10^{-6}$) is taken on the vertical axis is and time (second) is taken on the horizontal axis. As shown in FIG. 13, it is seen that the frequency changes little and is stable in the example 3-1, the example 3-2, and the example 3-3. In the comparative example 3-1, on the other hand, though no great change in the frequency is observed, it takes longer for the frequency to stabilize than in the example 3-1, the example 3-2, and the example 3-3. Further, in the comparative example 3-2, a great change in the frequency is observed and it takes much longer for the frequency to stabilize than in the example 3-1, the example 3-2, and the example 3-3. These experimental results are the results when the quartz resonator 24 was oscillated in the air atmosphere, but from the data obtained when the quartz resonator 24 was oscillated in the liquid in the above-described example 1, it was confirmed that adjusting the driving current to 0.2 mA stabilizes the frequency, and therefore, in the discussion, the experimental results shown in FIG. 12 can be associated as the results obtained when the quartz resonator 24 is oscillated in the liquid. Therefore, as shown in FIG. 12, when the driving current was set to 0.3 mA, the frequency was slightly disturbed after several ten seconds passed from the start of the measurement, but the frequency stabilizes thereafter, which leads to the understanding that setting the driving current of the quartz piece 20 to 0.3 mA or less is effective for accurate detection of the concentration of the substance to be sensed in the above-described sensing instrument. Incidentally, as for a lower limit value of the driving current, there is no limitation on the magnitude of the driving current, provided that the quartz resonator 24 normally oscillates. Therefore, defining the lower limit value of the driving current has no meaning.

The invention claimed is:

1. A sensing instrument for sensing a substance, adsorbed by an adsorption layer on an electrode at one face of a piezoelectric resonator, based on a change in a natural frequency of the piezoelectric resonator responsive to the substance, the piezoelectric resonator having said electrode at one face and another electrode at an opposite face, said substance being in a liquid which comes into contact with the adsorption layer, said substance being sensed based upon said change in said natural frequency, the sensing instrument comprising:

an oscillation circuit electrically coupled to said electrode and said another electrode that supplies the piezoelectric resonator with driving power using a drive current input to one of either said electrode or another electrode of at least 0.2 mA and no more than 0.3 mA to oscillate the piezoelectric resonator when the piezoelectric resonator is in contact with said liquid; and a measuring unit that measures a concentration of the substance to be sensed based on an oscillation output of said oscillation circuit, wherein an equivalent series resistance of said piezoelectric resonator when said piezoelectric resonator is in contact with said liquid is at least 150 ohms.

2. The sensing instrument according to claim 1, in which the drive current is less than 0.3 mA.

* * * * *